US012667553B2

(12) United States Patent
Feng et al.

(10) Patent No.: US 12,667,553 B2
(45) Date of Patent: Jun. 30, 2026

(54) APPLICATION OF MEDIUM-CHAIN FATTY ACID MIXED STRUCTURAL LIPID IN IMPROVING DIET-INDUCED DISORDERS OF GLUCOSE AND LIPID METABOLISM

(71) Applicant: Hangzhou Kangyuan Food Technology Co., LTD, Hangzhou (CN)

(72) Inventors: Fengqin Feng, Hangzhou (CN); Minjie Zhao, Hangzhou (CN); Xiyu Fu, Hangzhou (CN); Jing Wang, Hangzhou (CN); Liangyong Guo, Hangzhou (CN)

(73) Assignee: Hangzhou Kangyuan Food Technology Co., LTD, Hangzhou (CN)

( * ) Notice: Subject to any disclaimer, the term of this patent is extended or adjusted under 35 U.S.C. 154(b) by 0 days.

(21) Appl. No.: 19/215,283

(22) Filed: May 21, 2025

(65) Prior Publication Data

US 2026/0034089 A1     Feb. 5, 2026

(30) Foreign Application Priority Data

Aug. 5, 2024   (CN) .......................... 202411060266.5

(51) Int. Cl.
*A61K 31/23*      (2006.01)
*A61P 3/06*       (2006.01)
*A61P 3/08*       (2006.01)

(52) U.S. Cl.
CPC ................ *A61K 31/23* (2013.01); *A61P 3/06* (2018.01); *A61P 3/08* (2018.01)

(58) Field of Classification Search
CPC ............... A61K 31/23; A61P 3/08; A61P 3/06
See application file for complete search history.

(56) References Cited

U.S. PATENT DOCUMENTS

| | | | |
|---|---|---|---|
| 2003/0078298 A1 | 4/2003 | Rao et al. | |
| 2007/0281993 A1 | 12/2007 | Rozen | |
| 2018/0216144 A1 | 8/2018 | Rakitsky | |

FOREIGN PATENT DOCUMENTS

| | | |
|---|---|---|
| CN | 112772731 A | 5/2021 |
| CN | 113287659 A | 8/2021 |

*Primary Examiner* — Kevin E Weddington
(74) *Attorney, Agent, or Firm* — Hawaii Patent Services; Nathaniel K. Fedde; Kenton N. Fedde

(57)      ABSTRACT

The present disclosure provides an application of a medium-chain fatty acid mixed structural lipid in improving diet-induced disorders of glucose (Glu) and lipid metabolism. The medium-chain fatty acid mixed structural lipid includes capric lauric triglyceride and capric lauric diglyceride, and a mass percentage content ratio of capric acid to lauric acid in the medium-chain fatty acid mixed structure lipid is 1:1-1:4. In the present disclosure, it is found that adding medium-chain fatty acid mixed glyceride rich in lauric acid into high-energy feed can improve diet-induced disorders of Glu and lipid metabolism, including but not limited to reducing a serum Glu level, improving Glu homeostasis, reducing a serum low density lipoprotein cholesterol (LDL-C) level and improving expressions of genes related to Glu and lipid metabolism.

14 Claims, 9 Drawing Sheets

Pepck

G6pc

Gck

Pparg

Srebp1

1

APPLICATION OF MEDIUM-CHAIN FATTY ACID MIXED STRUCTURAL LIPID IN IMPROVING DIET-INDUCED DISORDERS OF GLUCOSE AND LIPID METABOLISM

CROSS-REFERENCE TO RELATED APPLICATION

This application claims priority of Chinese Patent Application No. 202411060266.5, filed on Aug. 5, 2024, the entire contents of which are incorporated herein by reference.

TECHNICAL FIELD

The present disclosure relates to the technical field of functional structural lipids, and in particular to an application of a medium-chain fatty acid mixed structural lipid rich in lauric acid in improving diet-induced disorders of glucose (Glu) and lipid metabolism.

BACKGROUND

With the improvement of living standard, people's dietary structure has undergone great changes, among which the proportion of high energy diet has increased significantly, resulting in excess energy intake, promoting adipocyte hypertrophy and fat ectopic deposition, and resulting in the disorder of Glu and lipid metabolism. Structural lipids refer to new types of lipids that are structurally modified by changing the composition and arrangement of fatty acids on the glycerol skeleton to enhance the physical and chemical properties thereof and nutritional value. Compared with natural lipids, structural oils can improve the physical and chemical properties of lipids, which is more conducive to the development and utilization of lipids. By synthesizing structural lipids, the content of functional fatty acids can be increased, and structural lipids can play better physiological functions. Studies have shown that structural lipids have positive effects on reducing fat accumulation and improving Glu and lipid metabolism.

Caprylic acid, capric acid and glycerol can react to obtain caprylic capric triglyceride (ODO), which is widely used in food. However, studies have shown that caprylic acid may have adverse effects on Glu and lipid metabolism, further aggravate the high-fat diet-induced blood Glu elevation and cholesterol metabolism disorder, and may also aggravate the changes in bone marrow microenvironment induced by obesity and promote bone metastasis of cancer.

SUMMARY

The present disclosure discovers that mixed glycerides of medium-chain fatty acids rich in lauric acid have effects on improving diet-induced disorders of Glu and lipid metabolism, including but not limited to reducing a serum Glu level, improving Glu homeostasis, reducing a serum low density lipoprotein cholesterol (LDL-C) level, and improving expressions of genes related to Glu and lipid metabolism.

Based on the discovery of the novel function of the mixed glycerides of medium-chain fatty acids rich in lauric acid in the present disclosure:

A first objective of the present disclosure is to provide an application of a medium-chain fatty acid mixed structural lipid in the preparation of health products or foods for improving diet-induced disorders of Glu and lipid metabolism, and the medium-chain fatty acid mixed structural lipid includes capric lauric triglyceride and capric lauric diglyceride.

A second objective of the present disclosure is to provide an application of the medium-chain fatty acid mixed structural lipid in the preparation of a feed for improving high-energy diet-induced disorders of Glu and lipid metabolism, and the medium-chain fatty acid mixed structural lipid includes capric lauric triglyceride and capric lauric diglyceride.

Aiming at the above two applications:

alternatively, a mass percentage content ratio of capric acid to lauric acid in the medium-chain fatty acid mixed structure lipid is 1:1 to 1:4. Further, a mass percentage content ratio of capric acid to lauric acid in the medium-chain fatty acid mixed structure lipid is 1:2 to 1:3.

Alternatively, the capric lauric triglyceride is monocapric dilauric triglyceride and dicaapric monolauric triglyceride; and the capric lauric diglyceride is monocapric monolauric diglyceride.

Alternatively, the monocapric dilauric triglyceride is at least one of 1-capric-2,3-dilaurin glycerol ester and 1,3-dilaurin-2-capric glycerol ester;

the dicaapric monolauric triglyceride is at least one of 1,2-dicaapric-3-laurin glycerol ester and 1,3-dicaapric-2-laurin glycerol ester; and the monocapric monolauric diglyceride is at least one of 1-capric-3-laurin diglyceride, 1-capric-2-laurin diglyceride and 2-capric-1-laurin diglyceride.

Alternatively, in percentage by mass, the medium-chain fatty acid mixed structure lipid includes:

monocapric dilauric triglyceride not less than 30%;

15-30% of dicaapric monolauric triglyceride; and 20-25% of monocapric monolauric diglyceride.

Alternatively, the improving diet-induced disorders of Glu and lipid metabolism includes at least one of a reduction in a serum Glu level, an improvement in Glu homeostasis, a reduction in serum LDL-C level, and an improvement in expressions of genes related to Glu and lipid metabolism.

Aiming at an application of the medium-chain fatty acid mixed structural lipid in the preparation of health products or foods:

alternatively, the medium-chain fatty acid mixed structural lipid can be directly added to foods or prepared into soft capsules as dietary supplements or health products, and a recommended daily intake is 0.25 g-2.30 g; more preferably, a recommended daily intake of the medium-chain fatty acid mixed structural lipid is 0.6 g-1.50 g; and optimally, a recommended daily intake of the medium-chain fatty acid mixed structural lipid is 0.8 g-1.2 g.

Aiming at an application of the medium-chain fatty acid mixed structural lipid as feed additives:

alternatively, the medium-chain fatty acid mixed structural lipid is added into a high-energy feed at an amount of 100-3000 mg/kg.

Further, the medium-chain fatty acid mixed structural lipid is added into the high-energy feed at an amount of 300-2500 mg/kg; further preferably, the medium-chain fatty acid mixed structural lipid is added to the high-energy feed at an amount of 800-1500 mg/kg; and optimally, the medium-chain fatty acid mixed structural lipid is added to the high-energy feed at an amount of 1000-1200 mg/kg.

Alternatively, the high-energy feed generally refers to a high-fat feed, a high-sugar feed or a high-fat and high-sugar feed, including a feed having a fat-to-energy ratio content of more than 35% and a fat-to-energy ratio in a range of 35-70%, or a feed including 60% fructose or sucrose; and further, the high-energy feed may be a high-fat feed having a fat-to-energy ratio of 45%.

The present disclosure also provides a medium-chain fatty acid mixed structural lipid, the medium-chain fatty acid mixed structural lipid includes capric lauric triglyceride and capric lauric diglyceride, and a mass percentage content ratio of capric acid to lauric acid in the medium-chain fatty acid mixed structure lipid is 1:1-1:4. Further, a mass percentage content ratio of capric acid to lauric acid in the medium-chain fatty acid mixed structure lipid is 1:2 to 1:3.

The present disclosure also provides a preparation method of the medium-chain fatty acid mixed structural lipid, including the following steps:

mixing the capric acid, the lauric acid and glycerol at 45-75° C., fully liquefying and evenly mixing, adding immobilized lipase or chemical catalyst, pumping vacuum or adding molecular sieves, maintaining heat reaction for 4-12 h, filtering and removing solids, removing unreacted fatty acid, glycerol and monoglyceride by molecular distillation or chemical separation method to obtain the medium-chain fatty acid mixed structural lipid.

Compared with the prior art, the present disclosure has the following beneficial effects.

According to the research of the present disclosure, ODO, the medium-chain fatty acid mixed structure lipid rich in lauric acid can significantly improve the high-energy diet-induced disorders of Glu metabolism, including but not limited to reducing the serum Glu level, improving the Glu homeostasis, reducing the serum LDL-C level and improving the expressions of genes related to Glu and lipid metabolism when compared with the medium-chain fatty acid mixed structure lipid rich in capric acid and other similar products, ODO.

DETAILED DESCRIPTION

Figure 1A:
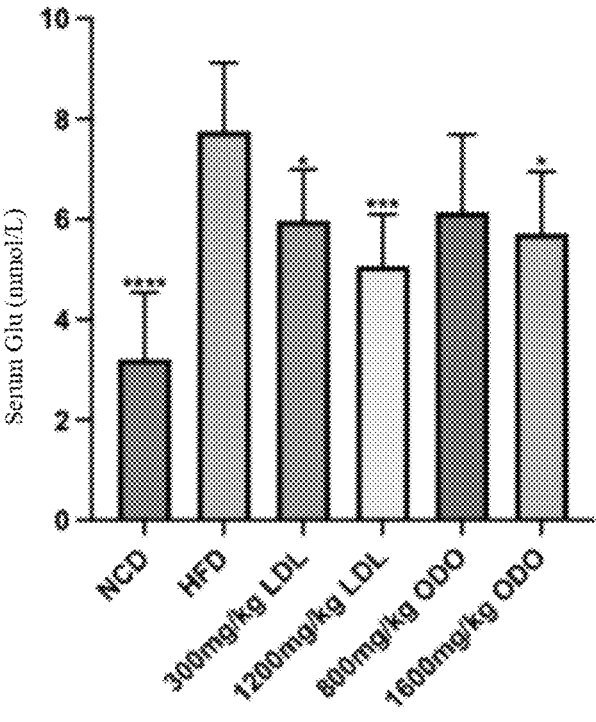
FIG. 1A shows the effects of different doses of a capric acid-lauric acid mixed structural lipid and ODO on serum Glu levels in mice fed with a high-fat diet.

Technical solutions in the examples of the present disclosure will be described clearly and completely in the following with reference to the attached drawings in the examples of the present disclosure. Obviously, all the described examples are only some, rather than all examples of the present disclosure. Based on the examples in the present disclosure, all other examples obtained by those ordinary skilled in the art without creative efforts belong to the protection scope of the present disclosure.

Unless otherwise defined, all technical and scientific terms used herein have the same meaning as commonly understood by those skilled in the art belonging to the present disclosure. The terms used herein in the specification of the present disclosure are only for the objective of describing specific examples and are not intended to limit the present disclosure.

The present disclosure provides a capric acid-lauric acid mixed structural lipid rich in lauric acid (LDL), having components of monocapric dilauric triglyceride, dicaapric monolauric triglyceride and monocapric monolauric diglyceride, and a mass percentage content ratio of capric acid to lauric acid in the capric acid-lauric acid mixed structural lipid is 1:1-1:4, more preferably 1:2-1:4.

The monocapric dilauric triglyceride is at least one of 1-capric-2,3-dilaurin glycerol ester and 1,3-dilaurin-2-capric glycerol ester; the dicaapric monolauric triglyceride is at least one of 1,2-dicaapric-3-laurin glycerol ester and 1,3-dicaapric-2-laurin glycerol ester; and the monocapric monolauric diglyceride includes at least one of 1-capric-3-laurin diglyceride, 1-capric-2-laurin diglyceride and 1-capric-2-laurin diglyceride.

A method for synthesizing the above-mentioned mixed structural lipid includes the following steps. Capric acid, lauric acid and glycerol are esterified to synthesize the capric acid-lauric acid mixed structural lipid. Esterification refers to a process in which fatty acids and alcohols react under a catalysis of acids, bases or enzymes to form ester compounds.

When the esterification occurs, a mixed molar ratio of capric acid, lauric acid and glycerol is 1:(1-8): 1. Preferably, a mixed molar ratio is 1:(2-4): 1, and the mixed structural lipid synthesized under this condition is rich in lauric acid.

When the esterification occurs, an immobilized lipase with substrate mass of 4-12% or a chemical catalyst with substrate mass of 0.2-0.8% is added. The immobilized lipase used is any one of immobilized *Aspergillus oryzae* lipase, *Rhizopus oryzae* lipase and *Rhizopus oryzae* lipase, and the chemical catalyst is a strong acid or a strong base.

The esterification includes the following steps. Reactants are mixed at 45-75° C., after fully liquefied and evenly mixed, immobilized lipase is added, vacuum is pumped or molecular sieve is added, and the reaction is kept at the temperature for 4-10 h, after solids are removed by filtration, fatty acid, glycerol and monoglyceride are removed by molecular distillation or chemical catalysis, and the capric acid-lauric acid mixed structural lipid is obtained.

An application of the mixed structural lipid in improving high-energy diet-induced disorders of Glu and lipid metabolism. In some examples, at least one of a reduction in a serum Glu level, an improvement in Glu homeostasis, a reduction in a serum LDL-C level, and an improvement in expressions of genes related to Glu and lipid metabolism needs to be fulfilled.

A capric acid-lauric acid mixed structural lipid rich in lauric acid (LDL) and a capric acid-lauric acid mixed structural lipid rich in capric acid (DLD) were synthesized by the above method, and tricaprin and trilaurin were directly mixed according to a fatty acid molar ratio of LDL to obtain a physical mixed oil (MLD), and ODO was a commercially available product. The efficacy of mixed structural lipids in improving diet-induced disorders of Glu and lipid metabolism was evaluated by animal experiments. C57BL/6J mice were randomly divided into six groups, 10 mice in each group, fed free diet and drank water, and samples were sampled after 16 weeks. A control group was fed with a normal diet (an energy supply ratio of fat was 10%), a high-energy group was fed with a high-fat diet (an energy supply ratio of fat was 45%), an experimental group 1 was fed with a high-fat diet supplemented with 300-2400 mg/kg of LDL, an experimental group 2 was fed with a high-fat diet supplemented with 300-2400 mg/kg of DLD, an experimental group 3 was fed with a high-fat diet supplemented with 300-2400 mg/kg of ODO, and an experimental group 4 was fed with a high-fat diet supplemented with 300-2400 mg/kg of MLD.

Specific examples are described below:

Example 1: Synthesis of Capric Acid-Lauric Acid Mixed Structural Lipid

Capric acid, lauric acid and glycerol were mixed according to a molar ratio of 1:2:1, placed in a 65° C. constant temperature water bath shaker, and completely melted and mixed, 10% immobilized lipase and appropriate amount of molecular sieve were added, a flip plug was covered, and the lipase and molecular sieve were removed by filtration after reacting at 200 rpm for 6 h. The product was dissolved in n-hexane, phenolphthalein was used as an indicator, a KOH methanol solution was titrated to pink, excess fatty acids were removed, and n-hexane was removed by rotary evaporation to obtain the LDL. A ratio of capric acid and lauric acid was changed (i.e., capric acid, lauric acid and glycerol were mixed in a molar ratio of 2:1:1), and the DLD was synthesized as described above. Appropriate amounts of the mixed structural lipids were weighed and identified by gas chromatography-mass spectrometry (GC-MS). The compositions are shown in Table 1 (LDL) and Table 2 (DLD).

TABLE 1

| Composition of LDL (capric acid:lauric acid = 1:2.3) | |
| --- | --- |
| Components | Assay % |
| 1,3-dilaurin-2-capric glycerol ester | 32.50 |
| 1,3-dicaapric-2-laurin glycerol ester | 15.55 |
| Tricaprin | 2.19 |
| 1-capric-3-laurin diglyceride | 20.43 |
| 1,2-dilaurin | 24.57 |
| 1,3-dicaprin | 4.30 |
| Lauric acid | 0.12 |
| Other | 0.34 |

TABLE 2

| Composition of DLD (capric acid:lauric acid = 1.7:1) | |
| --- | --- |
| Components | Assay % |
| 1,3-dicaapric-2-laurin glycerol ester | 25.64 |
| 1,3-dilaurin-2-capric glycerol ester | 13.17 |
| Tricaprin | 15.21 |
| 1-capric-3-laurin diglyceride | 18.92 |
| 1,3-dicaprin | 19.13 |
| 1,2-dilaurin | 3.52 |
| Monocaprin | 1.13 |
| Monolaurin | 0.67 |
| Capric acid | 1.44 |
| Lauric acid | 1.16 |
| Other | 0.01 |

Example 2: Amelioration of High-Fat Diet-Induced Disorders of Glu and Lipid Metabolism by Capric Acid-Lauric Acid Mixed Structural Lipids C57BL/6J mice were randomly divided into eight groups, 10 mice in each group, and fed free diet and drank water; a normal control diet (NCD) group was fed with the common diet (an energy supply ratio of fat was 10%), a high-fat diet (HFD) group was fed with the high-fat diet (an energy supply ratio of fat was 45%), the experimental groups were fed with LDL at 300 and 1200 mg/kg (Table 1), DLD at 1200 mg/kg (Table 2) and MLD, and ODO at 800 and 1600 mg/kg respectively. After 14 weeks of feeding, the mice were fasted overnight and Glu tolerance was determined. Blood was taken from the tail vein to measure fasting blood Glu, which was recorded as blood Glu at 0 min, and Glu solution (Glu amount was 2 g/kg of body weight) was injected intraperitoneally. After 30, 60, 90 and 120 min, blood was taken from the tail vein to measure the blood Glu value, and the blood Glu curve was drawn and an AUC was calculated. After 16 weeks, the mice were fasted overnight, and fresh blood was collected from the orbit. After standing for 30 min, the serum was centrifuged and stored at −80° C. The levels of serum Glu and lipid metabolism related indicators were determined by commercially available kits.

Figure 1B:
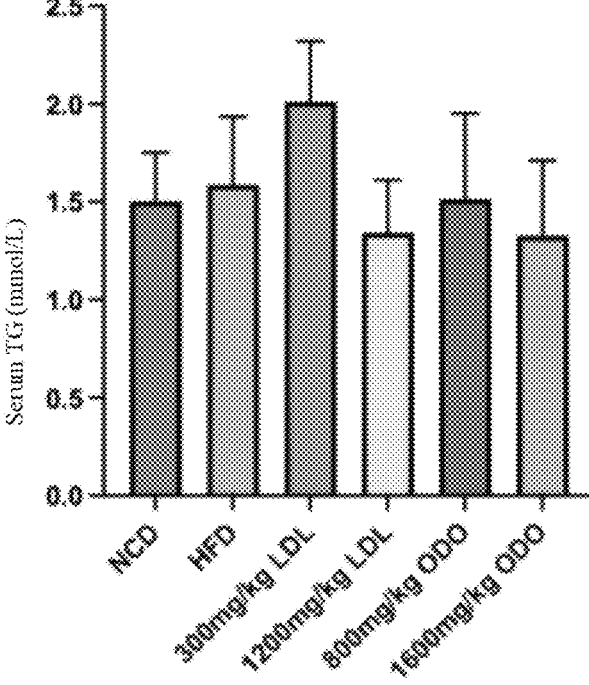
FIG. 1B shows the effects of different doses of the capric acid-lauric acid mixed structural lipid and ODO on serum total triglyceride (TG) in the mice fed with the high-fat diet.
Figure 1C:
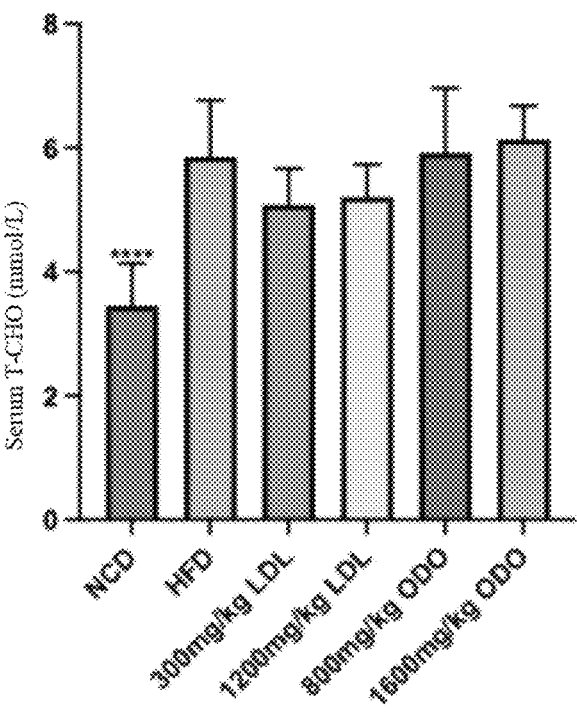
FIG. 1C shows the effects of different doses of the capric acid-lauric acid mixed structural lipid and ODO on serum total cholesterol (T-CHO) in the mice fed with the high-fat diet.
Figure 1D:
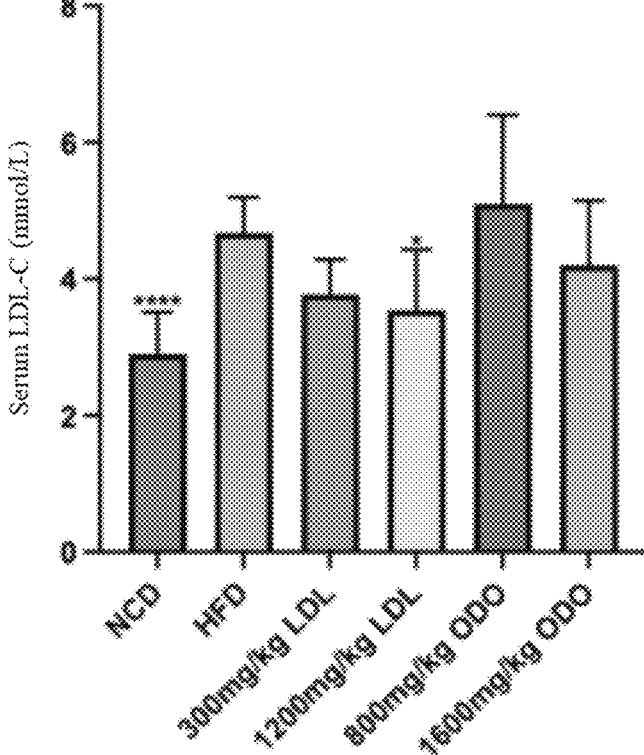
FIG. 1D shows the effects of different doses of the capric acid-lauric acid mixed structural lipid and ODO on serum LDL-C in the mice fed with the high-fat diet.
Figure 1E:
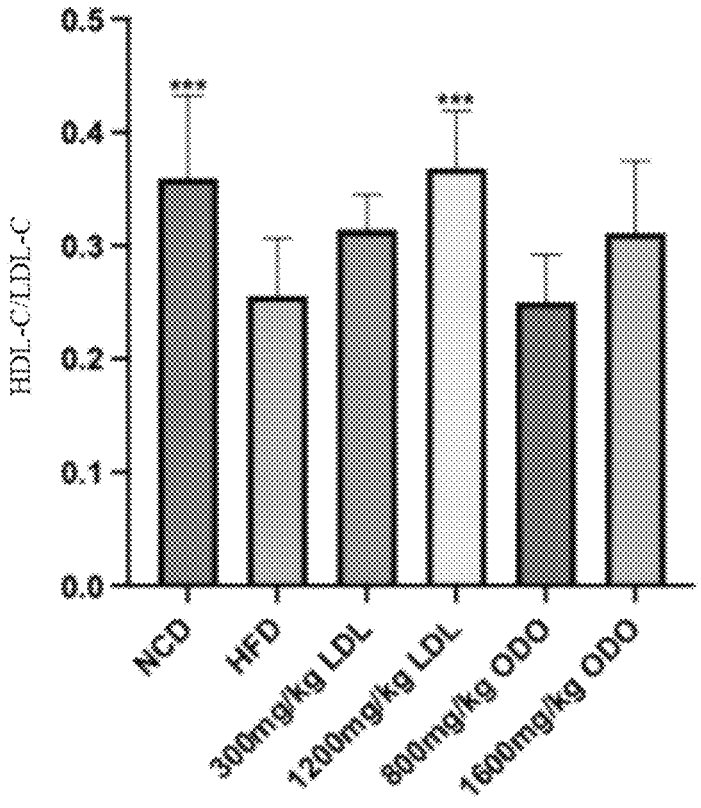
FIG. 1E shows the effects of different doses of the capric acid-lauric acid mixed structural lipid and ODO on a ratio of high density lipoprotein cholesterol (HDL-C) to LDL-C in serum of the mice fed with the high-fat diet.

The results of serum Glu and lipid metabolism-related indicators in mice gavaged with different doses of LDL and ODO (FIGS. 1A-1E) showed that the effect of 1200 mg/kg LDL in improving serum Glu (FIG. 1A), serum LDL-C(FIG. 1D) and HDL-C/LDL-C ratio (FIG. 1E) was significantly stronger than that of 300 mg/kg LDL; and the effect of 1600 mg/kg ODO on reducing serum Glu was significantly stronger than that of 800 mg/kg ODO, and the effect of reducing serum LDL-C was stronger than that of 800 mg/kg ODO (p=0.0846). Levels of serum total triglycerides (TG) (FIG. 1B) and serum total cholesterol (T-CHO) (FIG. 1C) were not significantly different among the groups, serum TG levels of 300 mg/kg LDL and 800 mg/kg ODO were slightly higher than those of 1200 mg/kg LDL and 1600 mg/kg ODO.

The comparison shows the following.

(1) The effect of 1200 mg/kg LDL in improving Glu and lipid metabolism is better than that of 300 mg/kg LDL, and the effect of 1600 mg/kg ODO in improving Glu and lipid metabolism is better than that of 800 mg/kg ODO. Within a certain range, the effects of LDL and ODO in improving Glu and lipid metabolism increase with the increase of the addition amount thereof.

(2) The effect of 300 mg/kg LDL in improving Glu and lipid metabolism is close to that of 1600 mg/kg ODO.

(3) The effect of 1200 mg/kg LDL in improving Glu and lipid metabolism is significantly better than that of 1600 mg/kg ODO.

It shows that the capric acid-lauric acid structural lipid can achieve better efficacy in improving diet-induced disorders of Glu and lipid metabolism than ODO at lower doses.

Figures 2A, 2B:
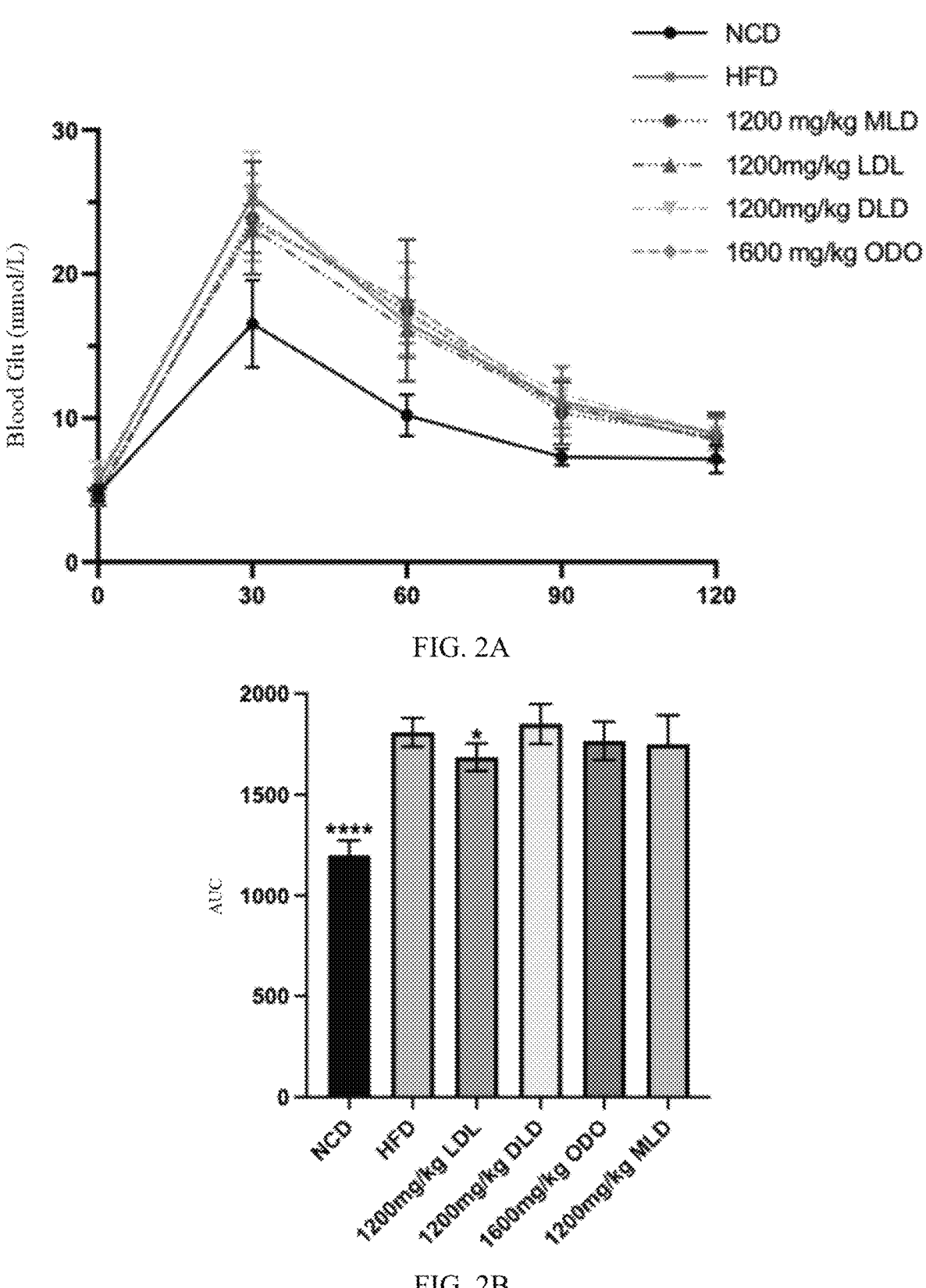
FIG. 2A shows the effects of the capric acid-lauric acid mixed structural lipid on intraperitoneal Glu tolerance in the mice fed with the high-fat diet.
FIG. 2B shows the effects of the capric acid-lauric acid mixed structural lipid on an area under curve (AUC) of intraperitoneal glucose tolerance in the mice fed with the high-fat diet.
Figure 2C:
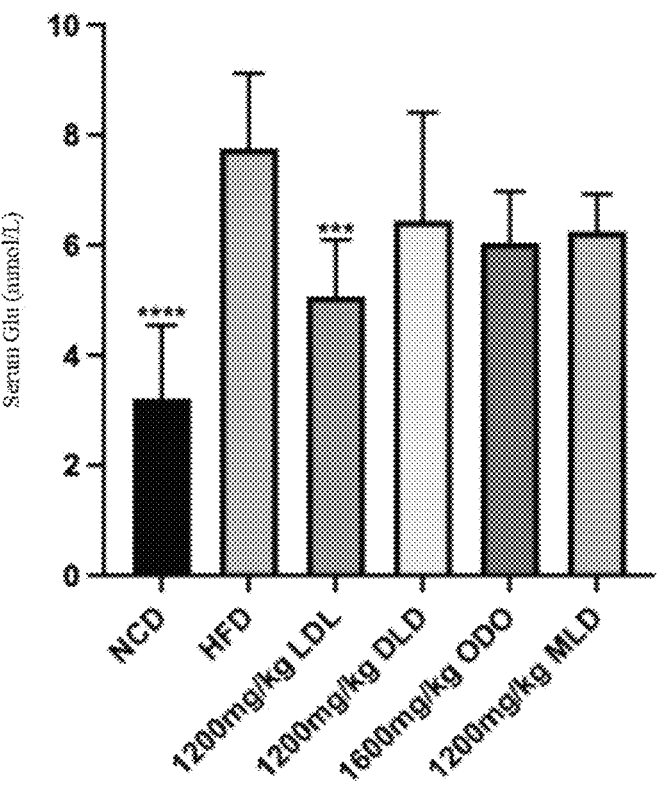
FIG. 2C shows the effects of the capric acid-lauric acid mixed structural lipid on serum Glu levels in the mice fed with the high-fat diet.
Figure 3A:
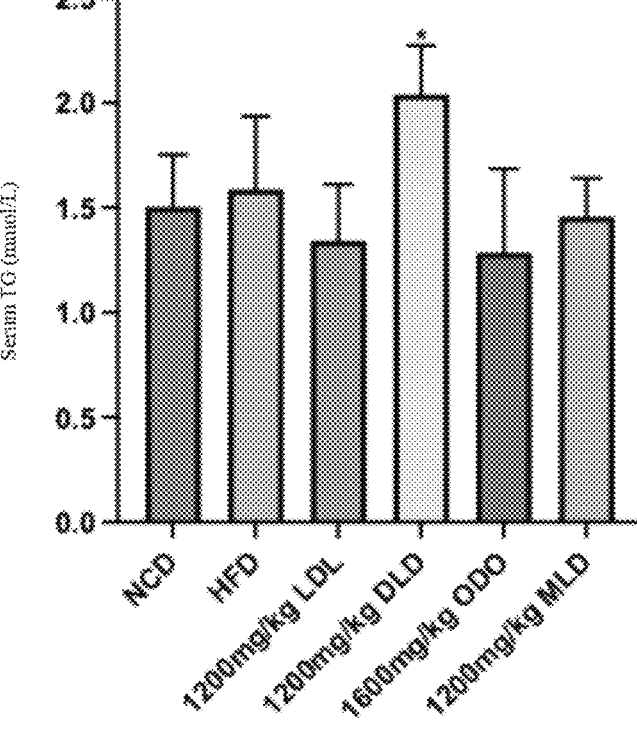
FIG. 3A shows the effects of the capric acid-lauric acid mixed structural lipid on serum TG in the mice fed with the high-fat diet.
Figure 3B:
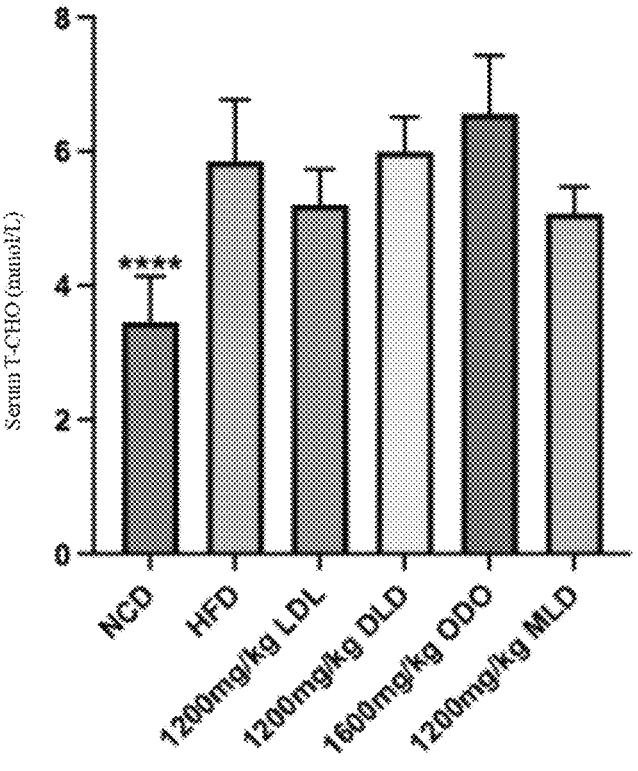
FIG. 3B shows the effects of the capric acid-lauric acid mixed structural lipid on serum T-CHO in the mice fed with the high-fat diet.
Figure 3C:
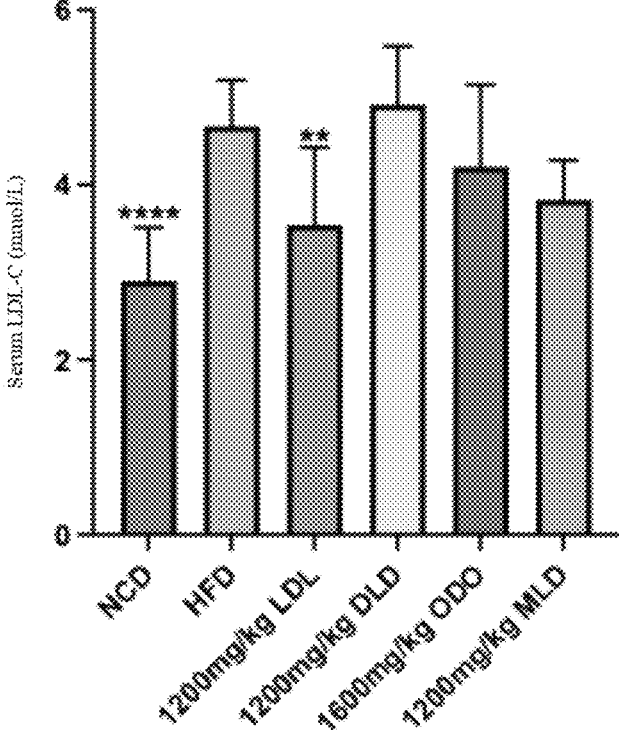
FIG. 3C shows the effects of the capric acid-lauric acid mixed structural lipid on serum LDL-C in the mice fed with the high-fat diet.
Figure 3D:
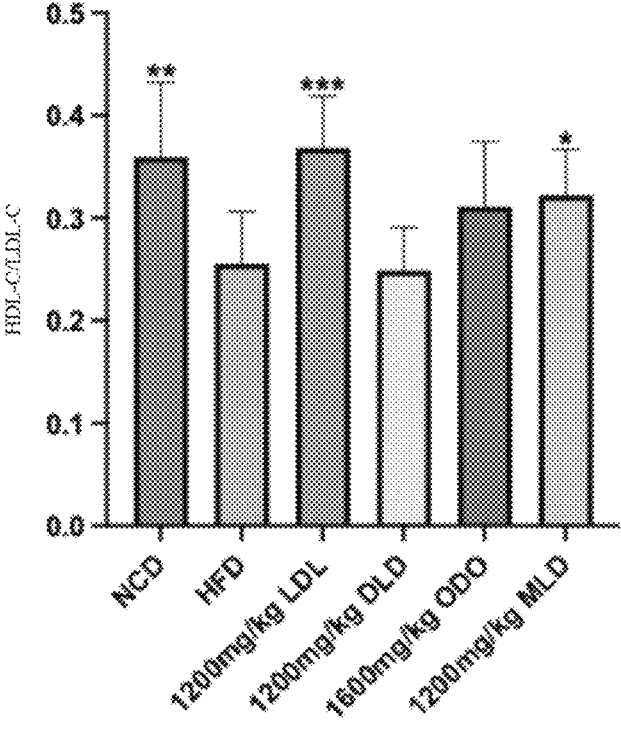
FIG. 3D shows the effects of the capric acid-lauric acid mixed structural lipid on a ratio of HDL-C to LDL-C in serum of the mice fed with the high-fat diet.
Figure 4A:
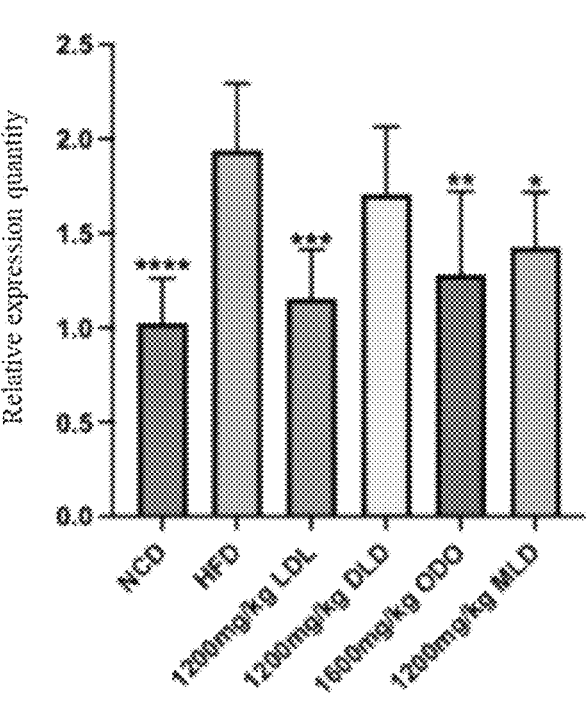
FIG. 4A shows the effects of the capric acid-lauric acid mixed structural lipid on the expression of hepatic phosphoenolpyruvate carboxykinase (PEPCK) gene in the mice fed with the high-fat diet.
Figure 4B:
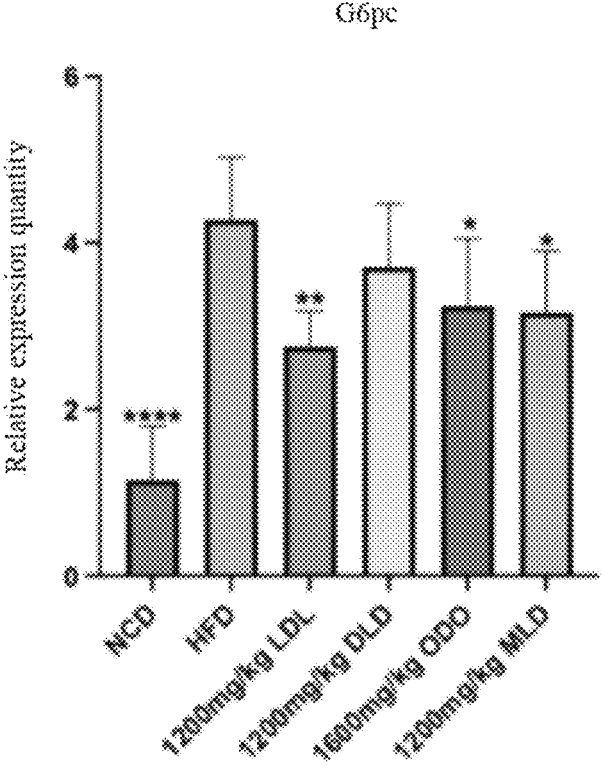
FIG. 4B shows the effects of the capric acid-lauric acid mixed structural lipid on the expression of hepatic glucose-6-phosphatase catalytic subunit (G6PC) gene in the mice fed with the high-fat diet.
Figure 4C:
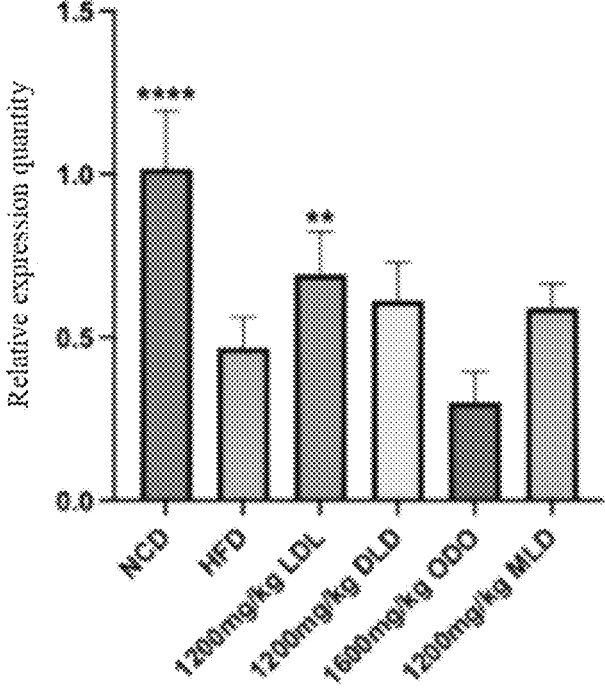
FIG. 4C shows the effects of the capric acid-lauric acid mixed structural lipid on the expression of hepatic hexokinase (HK) gene in the mice fed with the high-fat diet.
Figure 4D:
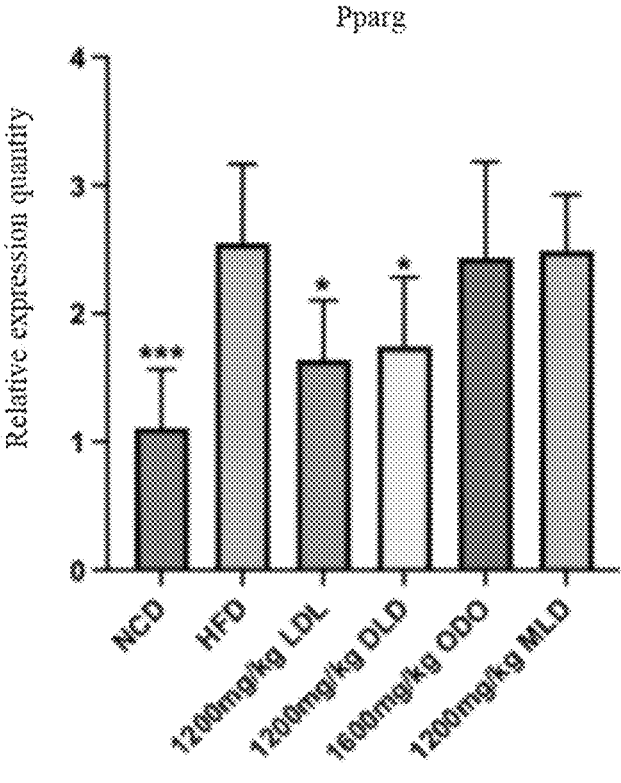
FIG. 4D shows the effects of the capric acid-lauric acid mixed structural lipid on the expression of hepatic peroxisome proliferator-activated receptor γ (PPARγ) gene in the mice fed with the high-fat diet.
Figure 4E:
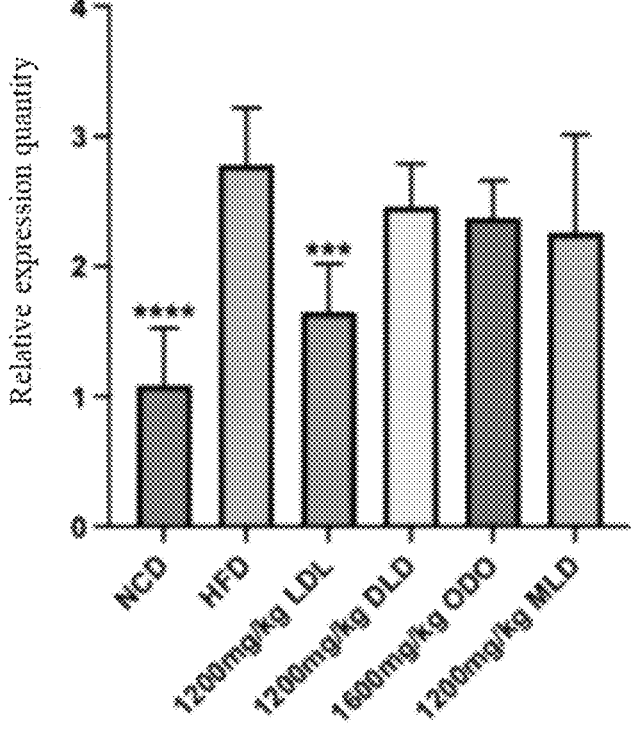
FIG. 4E shows the effects of the capric acid-lauric acid mixed structural lipid on the expression of hepatic sterol regulatory element-binding protein 1 (SREBP-1) gene in the mice fed with the high-fat diet.

The results of Glu tolerance test showed (FIG. 2A and FIG. 2B) that there was no significant difference in initial blood Glu among each group. 30, 60 and 90 min after intraperitoneal injection of Glu, the blood Glu of all groups fed with high-fat diet was higher than that of the NCD group, and the blood Glu of all groups recovered to a similar level after 120 min. Statistical analysis of the AUC showed that the AUC of each group fed with high-fat diet was significantly higher than that of the NCD group. DLD, ODO and MLD had no obvious effect on this, while the AUC of the LDL group was significantly lower than that of the HFD group, which indicated that LDL could improve the disruption of Glu homeostasis induced by high-fat diet. The results of serum Glu levels are shown in FIG. 2C. LDL can significantly reduce high-fat diet-induced blood Glu increase, and ODO (p=0.0521) and MLD (p=0.0744) have a tendency to reduce blood Glu, but not significantly.

The effects of capric acid-lauric acid mixed structural lipids on serum lipid metabolism-related indicators are shown in FIGS. 3A-3D. Serum TG levels (FIG. 3A) in each group were not significantly different, but DLD further increased the serum TG levels. High-fat diet increased the levels of serum T-CHO (FIG. 3B) and serum LDL-C(FIG. 3C), LDL, DLD, and MDL had no obvious effect on serum T-CHO levels, and ODO had a tendency to further increase serum T-CHO (p=0.099). MLD could reduce LDL-C to some extent (p=0.068), but not significantly, and LDL significantly reduced serum LDL-C levels. From the results of the ratio of HDL-C/LDL-C(FIG. 3D), DLD and ODO have no obvious improvement effect on this, MLD and LDL can increase serum HDL-C/LDL-C, and the effect of LDL is more significant. The above results indicate that LDL has a good effect on regulating serum lipid metabolism.

The effect of capric acid-lauric acid mixed structural lipids on the expression of genes related to liver Glu and lipid metabolism is shown in FIGS. 4A-4E. High-fat diet increased the expression of Glu-6-phosphatase catalytic subunit gene (G6pc) (FIG. 4B) and phosphoenolpyruvate carboxykinase gene (Pepck) (FIG. 4A) related to gluconeogenesis in liver. The expressions of Gopc and Pepck in liver of each experimental group were lower than those in the HFD group, LDL, ODO and MLD were significantly different, and the effect of LDL was the most significant. LDL significantly improved the decrease of glucokinase gene (Gck) expression in liver induced by high-fat diet, DLD and MLD had no obvious effect on this, and ODO may further decrease the expression of Gck in liver (p=0.099). Peroxisome proliferator-activated receptor γ gene (Pparg) (FIG. 4D) and sterol regulatory element binding protein 1 gene (Srebp1) were related to lipid synthesis. LDL significantly down-regulated the expression of Pparg and Srebp1 in liver of mice fed with high-fat diet, DLD only reduced the expression of Pparg, and ODO and MLD had no significant effect on the expression of Pparg and Srebp1 in liver.

In conclusion, compared with MLD, LDL significantly reduced serum Glu levels, improved the expression of genes related to Glu homeostasis and liver lipid metabolism, and improved the expression of genes related to cholesterol metabolism and liver Glu metabolism more significantly, indicating that the improvement of structured lipids on Glu and lipid metabolism was better than that of triglyceride physical mixed oil. Compared with DLD, LDL significantly reduced serum Glu levels, improved Glu homeostasis and cholesterol metabolism, and improved the expression of genes related to liver Glu and lipid metabolism more significantly, indicating that LDL was better than DLD in improving Glu and lipid metabolism.

Compared with ODO supplemented with 1600 mg/kg, LDL supplementation was lower (1200 mg/kg), and significantly reduced serum Glu levels, improved the expression of genes related to Glu homeostasis, cholesterol metabolism and liver lipid metabolism, and had a more significant effect in improving the expression of genes related to liver Glu metabolism, indicating that capric acid-lauric acid structural lipids could achieve better effect of improving diet-induced disorders of Glu and lipid metabolism than ODO at a lower dosage.

The above results show that the LDL can improve Glu homeostasis, regulate cholesterol metabolism, reduce lipid synthesis in liver, and improve the disorders of Glu and lipid metabolism induced by high-fat diet. It is expected to be used in foods or health products for improving the disorders of Glu and lipid metabolism.

The above-described examples only express a few embodiments of the present disclosure, and the description thereof is relatively specific and detailed, but are not to be construed as limiting the scope of the present disclosure. It is to be pointed out that for those skilled in the art, several modifications and improvements can be made without departing from the concept of the present disclosure, and these are all within the scope of protection of the present disclosure. Therefore, the scope of protection of the present disclosure is to be determined by the appended claims.

The invention claimed is:

1. A medium-chain fatty acid mixed structural lipid, comprising capric lauric triglyceride and capric lauric diglyceride, wherein a mass percentage content ratio of capric acid to lauric acid in the medium-chain fatty acid mixed structure lipid is 1:1-1:4;

the capric lauric triglyceride is monocapric dilauric triglyceride and dicaapric monolauric triglyceride; and the capric lauric diglyceride is monocapric monolauric diglyceride;

in percentage by mass, the medium-chain fatty acid mixed structural lipid comprises:

monocapric dilauric triglyceride not less than 30%;

15-30% of dicaapric monolauric triglyceride; and 20-25% of monocapric monolauric diglyceride; and wherein preparation of the medium-chain fatty acid mixed structural lipid comprises:

mixing the capric acid, the lauric acid and glycerol at 45-75° C., fully liquefying and evenly mixing a mixture, adding immobilized lipase or a chemical catalyst, pumping vacuum or adding molecular sieves, maintaining heat reaction for 4-12 h, filtering and removing solids, and removing unreacted fatty acid, glycerol and monoglyceride by molecular distillation or a chemical method to obtain the medium-chain fatty acid mixed structural lipid.

2. The medium-chain fatty acid mixed structure lipid according to claim 1, wherein, the monocapric dilauric triglyceride is at least one of 1-capric-2,3-dilaurin glycerol ester and 1,3-dilaurin-2-capric glycerol ester;

the dicaapric monolauric triglyceride is at least one of 1,2-dicaapric-3-laurin glycerol ester and 1,3-dicaapric-2-laurin glycerol ester; and the monocapric monolauric diglyceride is at least one of 1-capric-3-laurin diglyceride, 1-capric-2-laurin diglyceride and 2-capric-1-laurin diglyceride.

3. A food additive for treating Glu homeostasis, regulating cholesterol metabolism, reducing lipid synthesis in liver, and improving disorders of Glu and lipid metabolism induced by high-fat diet wherein the food additive comprises the medium-chain fatty acid mixed structural lipid according to claim 1.

4. A food additive for treating Glu homeostasis, regulating cholesterol metabolism, reducing lipid synthesis in liver, and improving disorders of Glu and lipid metabolism induced by high-fat diet wherein the food additive comprises the medium-chain fatty acid mixed structural lipid according to claim 2.

5. A high-energy feed for administration to a subject wherein the high-energy feed comprises the food additive according to claim 3.

6. A high-energy feed for administration to a subject wherein the high-energy feed comprises the food additive according to claim 4.

7. A method of using a medium-chain fatty acid mixed structural lipid comprising:

providing a medium-chain fatty acid mixed structural lipid according to claim 1; and adding the medium-chain fatty acid mixed structural lipid to a health care product or food.

8. A method of using a medium-chain fatty acid mixed structural lipid comprising:

providing a medium-chain fatty acid mixed structural lipid according to claim 2; and adding the medium-chain fatty acid mixed structural lipid to a health care product or food.

9. The method according to claim 7 wherein the health care product comprises a soft capsule.

10. The method according to claim 8, wherein the health care product comprises a soft capsule.

11. The high-energy feed according to claim 5, wherein the high energy feed has a fat-to-energy ratio in a range of 35-70%.

12. The high-energy feed according to claim 5, wherein the high energy feed has a fat-to-energy ratio of 45%.

13. The high-energy feed according to claim 6, wherein the high energy feed has a fat-to-energy ratio in a range of 35-70%.

14. The high-energy feed according to claim 6, wherein the high energy feed has a fat-to-energy ratio of 45%.

* * * * *